(12) United States Patent
Parramon et al.

(10) Patent No.: US 11,259,732 B2
(45) Date of Patent: Mar. 1, 2022

(54) METHOD AND DEVICE FOR ACQUIRING PHYSIOLOGICAL DATA DURING TISSUE STIMULATION PROCEDURE

(71) Applicant: Boston Scientific Neuromodulation Corporation, Valencia, CA (US)

(72) Inventors: Jordi Parramon, Valencia, CA (US); Emanuel Feldman, Simi Valley, CA (US); Jess Weiqian Shi, Porter Ranch, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 244 days.

(21) Appl. No.: 16/292,529

(22) Filed: Mar. 5, 2019

(65) Prior Publication Data

US 2019/0192848 A1 Jun. 27, 2019

Related U.S. Application Data

(60) Continuation of application No. 15/195,162, filed on Jun. 28, 2016, now Pat. No. 10,252,049, which is a
(Continued)

(51) Int. Cl.
*A61B 5/24* (2021.01)
*A61B 5/053* (2021.01)
(Continued)

(52) U.S. Cl.
CPC .............. *A61B 5/24* (2021.01); *A61B 5/053* (2013.01); *A61B 5/0538* (2013.01);
(Continued)

(58) Field of Classification Search
CPC ......... A61B 5/053; A61B 5/0538; A61B 5/24; A61N 1/0551; A61N 1/36071; A61N 1/3614; A61N 1/36164; A61N 1/37235
See application file for complete search history.

(56) References Cited

U.S. PATENT DOCUMENTS

| | | | |
|---|---|---|---|
| 4,059,116 A | * | 11/1977 | Adams ................. A61N 1/3622 607/9 |
| 4,255,790 A | | 3/1981 | Hondeghem |
| | | | (Continued) |

OTHER PUBLICATIONS

"U.S. Appl. No. 12/825,187, Advisory Action dated Feb. 7, 2013", 3 pgs.
(Continued)

*Primary Examiner* — Christopher A Flory
(74) *Attorney, Agent, or Firm* — Schwegman Lundberg & Woessner, P.A.

(57) ABSTRACT

A method and system of providing therapy to a patient implanted with an array of electrodes is provided. A train of electrical stimulation pulses is conveyed within a stimulation timing channel between a group of the electrodes to stimulate neural tissue, thereby providing continuous therapy to the patient. Electrical parameter is sensed within a sensing timing channel using at least one of the electrodes, wherein the first stimulation timing channel and sensing timing channel are coordinated, such that the electrical parameter is sensed during the conveyance of the pulse train within time slots that do not temporally overlap any active phase of the stimulation pulses.

20 Claims, 8 Drawing Sheets

Related U.S. Application Data division of application No. 12/825,187, filed on Jun. 28, 2010, now Pat. No. 9,399,132.

(60) Provisional application No. 61/221,987, filed on Jun. 30, 2009.

(51) Int. Cl.
  *A61N 1/36* (2006.01)
  *A61B 5/0538* (2021.01)
  *A61N 1/05* (2006.01)
  *A61N 1/372* (2006.01)

(52) U.S. Cl.
  CPC ......... *A61N 1/0551* (2013.01); *A61N 1/3614* (2017.08); *A61N 1/36164* (2013.01); *A61N 1/37235* (2013.01); *A61N 1/36071* (2013.01)

(56) References Cited

U.S. PATENT DOCUMENTS

| | | | |
|---|---|---|---|
| 4,453,547 A | 6/1984 | Castel | |
| 4,572,193 A | 2/1986 | Mann et al. | |
| 4,788,980 A | 12/1988 | Mann et al. | |
| 4,825,870 A * | 5/1989 | Mann | A61N 1/368 607/9 |
| 5,188,106 A | 2/1993 | Nappholz et al. | |
| 5,251,621 A | 10/1993 | Collins | |
| 5,269,299 A | 12/1993 | Duncan | |
| 5,312,445 A | 5/1994 | Nappholz et al. | |
| 5,318,591 A | 6/1994 | Causey, III et al. | |
| 5,330,509 A | 7/1994 | Kroll et al. | |
| 5,941,906 A | 8/1999 | Barreras, Sr. et al. | |
| 6,112,119 A | 8/2000 | Schuelke et al. | |
| 6,458,157 B1 | 10/2002 | Suaning | |
| 6,516,227 B1 | 2/2003 | Meadows et al. | |
| 6,572,543 B1 | 6/2003 | Christopherson et al. | |
| 6,895,280 B2 | 5/2005 | Meadows et al. | |
| 6,993,384 B2 | 1/2006 | Bradley et al. | |
| 7,123,961 B1 | 10/2006 | Kroll et al. | |
| 7,239,920 B1 | 7/2007 | Thacker et al. | |
| 7,317,948 B1 | 1/2008 | King et al. | |
| 7,539,538 B2 | 5/2009 | Parramon et al. | |
| 9,126,044 B2 | 9/2015 | Kramer et al. | |
| 9,399,132 B2 | 7/2016 | Parramon et al. | |
| 9,504,833 B2 | 11/2016 | Kramer et al. | |
| 9,782,591 B2 | 10/2017 | Kramer et al. | |
| 2003/0139781 A1 | 7/2003 | Bradley et al. | |
| 2003/0204225 A1* | 10/2003 | Heathershaw | A61N 1/36125 607/48 |
| 2004/0049235 A1* | 3/2004 | Deno | A61N 1/36031 607/9 |
| 2005/0059897 A1* | 3/2005 | Snell | A61N 1/371 600/510 |
| 2005/0060002 A1* | 3/2005 | Zhu | A61N 1/36542 607/19 |
| 2005/0115561 A1 | 6/2005 | Stahmann et al. | |
| 2005/0240240 A1 | 10/2005 | Park et al. | |
| 2005/0267542 A1 | 12/2005 | David et al. | |
| 2005/0267546 A1 | 12/2005 | Parramon et al. | |
| 2006/0149328 A1* | 7/2006 | Parikh | A61N 1/3627 607/28 |
| 2006/0149345 A1 | 7/2006 | Boggs, II et al. | |
| 2006/0173507 A1 | 8/2006 | Mrva et al. | |
| 2006/0217781 A1* | 9/2006 | John | G16H 50/50 607/45 |
| 2006/0224222 A1 | 10/2006 | Bradley | |
| 2006/0247699 A1* | 11/2006 | Burnes | A61N 1/3627 607/9 |
| 2006/0247701 A1 | 11/2006 | Zacouto | |
| 2007/0043401 A1* | 2/2007 | John | G16H 50/50 607/45 |
| 2007/0198066 A1 | 8/2007 | Greenberg et al. | |
| 2007/0233194 A1 | 10/2007 | Craig | |
| 2007/0299477 A1* | 12/2007 | Kleckner | A61N 1/36585 607/9 |
| 2008/0046025 A1 | 2/2008 | Tass | |
| 2008/0091240 A1 | 4/2008 | Ben-David et al. | |
| 2009/0024189 A1* | 1/2009 | Lee | A61N 1/3787 607/66 |
| 2009/0157155 A1* | 6/2009 | Bradley | A61N 1/37247 607/116 |
| 2010/0010387 A1 | 1/2010 | Skelton et al. | |
| 2010/0114224 A1 | 5/2010 | Krause et al. | |
| 2010/0114260 A1* | 5/2010 | Donofrio | A61N 1/0551 607/72 |
| 2010/0152804 A1* | 6/2010 | Kleckner | A61N 1/36114 607/17 |
| 2010/0331916 A1 | 12/2010 | Parramon et al. | |
| 2012/0303084 A1* | 11/2012 | Kleckner | A61N 1/3684 607/25 |
| 2016/0303368 A1 | 10/2016 | Parramon et al. | |
| 2017/0319855 A1 | 11/2017 | Kramer et al. | |

OTHER PUBLICATIONS

"U.S. Appl. No. 12/825,187, Appeal Decision mailed Dec. 9, 2015", 5 pgs.

"U.S. Appl. No. 12/825,187, Examiner's Answer dated May 31, 2013", 6 pgs.

"U.S. Appl. No. 12/825,187, Final Office Action dated Dec. 4, 2012", 6 pgs.

"U.S. Appl. No. 12/825,187, Non Final Office Action dated Jul. 25, 2012", 10 pgs.

"U.S. Appl. No. 12/825,187, Notice of Allowance dated Mar. 23, 2016", 5 pgs.

"U.S. Appl. No. 12/825,187, Reply Brief filed Jul. 17, 2013", 5 pgs.

"U.S. Appl. No. 12/825,187, Response filed Jan. 22, 2013 to Final Office Action dated Dec. 4, 2012", 4 pgs.

"U.S. Appl. No. 12/825,187, Response filed May 29, 2012 to Restriction Requirement dated May 1, 2012", 6 pgs.

"U.S. Appl. No. 12/825,187, Response filed Oct. 22, 2012 to Non Final Office Action dated Jul. 25, 2012", 14 pgs.

"U.S. Appl. No. 12/825,187, Restriction Requirement dated May 1, 2012", 6 pgs.

"U.S. Appl. No. 15/195,162, Examiner Interview Summary dated Nov. 8, 2018", 2 pgs.

"U.S. Appl. No. 15/195,162, Non Final Office Action dated Jul. 10, 2018", 12 pgs.

"U.S. Appl. No. 15/195,162, Notice of Allowance dated Nov. 26, 2018", 11 pgs.

"U.S. Appl. No. 15/195,162, Preliminary Amendment filed Jun. 29, 2016", 8 pgs.

"U.S. Appl. No. 15/195,162, Response filed Jun. 19, 2018 to Restriction Requirement Action dated Apr. 20, 2018", 6 pgs.

"U.S. Appl. No. 15/195,162, Response filed Oct. 10, 2018 to Non Final Office Action dated Jul. 10, 2018", 10 pgs.

"U.S. Appl. No. 15/195,162, Restriction Requirement dated Apr. 20, 2018", 6 pgs.

* cited by examiner

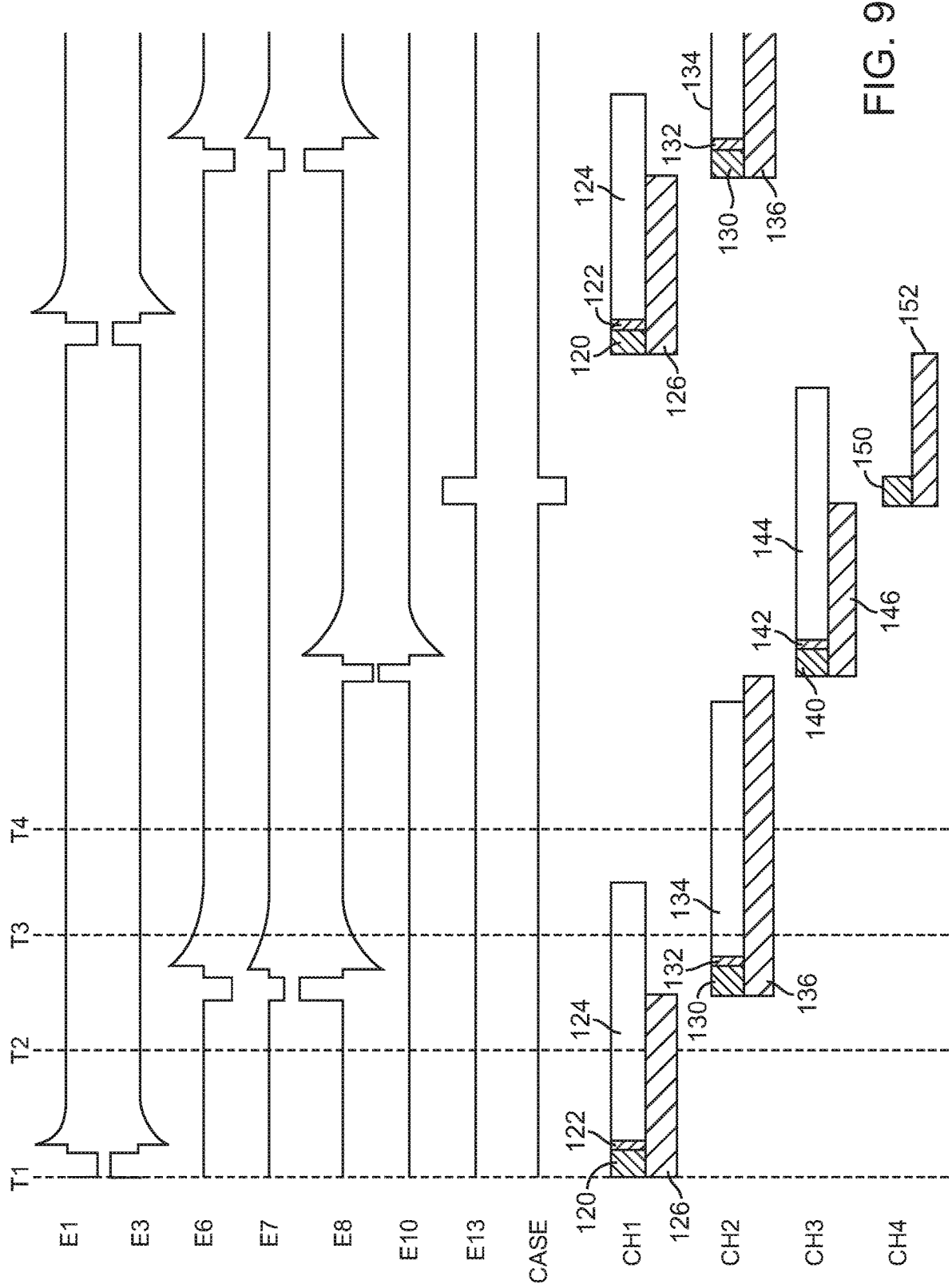

METHOD AND DEVICE FOR ACQUIRING PHYSIOLOGICAL DATA DURING TISSUE STIMULATION PROCEDURE

RELATED APPLICATION

The present application is a continuation of U.S. application Ser. No. 15/195,162, filed Jun. 28, 2016, now issued as U.S. Pat. No. 10,252,049, which is a divisional of U.S. application Ser. No. 12/825,187, filed Jun. 28, 2010, now issued as U.S. Pat. No. 9,399,132, which claims the benefit under 35 U.S.C. § 119 to U.S. provisional patent application Ser. No. 61/221,987, filed Jun. 30, 2009. The foregoing applications are hereby incorporated by reference into the present application in their entirety.

FIELD OF THE INVENTION

The present invention relates to tissue stimulation systems, and more particularly, to a system and method for sensing information during a stimulation procedure.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes an electrode lead implanted at the desired stimulation site and an implantable pulse generator (IPG) implanted remotely from the stimulation site, but coupled either directly to the electrode lead or indirectly to the electrode lead via a lead extension. Thus, electrical pulses can be delivered from the neurostimulator to the stimulation electrode(s) to stimulate or activate a volume of tissue in accordance with a set of stimulation parameters and provide the desired efficacious therapy to the patient. A typical stimulation parameter set may include the electrodes that are sourcing (anodes) or returning (cathodes) the stimulation current at any given time, as well as the amplitude, duration, rate, and burst rate of the stimulation pulses.

The neurostimulation system may further comprise a handheld remote control (RC) to remotely instruct the neurostimulator to generate electrical stimulation pulses in accordance with selected stimulation parameters. The RC may, itself, be programmed by a technician attending the patient, for example, by using a Clinician's Programmer (CP), which typically includes a general purpose computer, such as a laptop, with a programming software package installed thereon.

The use of sensed electrical information, such as, e.g., impedance, field potential neural activity, etc., is of increasing importance in neurostimulation applications, such as SCS, which may some day provide intelligent and autonomous closed-loop control of the neurostimulation, thereby reducing the direct involvement of the patient in managing the therapy. With respect to SCS, there are currently two limitations that make sensing of electrical parameter information to achieve on-the-fly closed-loop stimulation control difficult to accomplish: (1) the sensing of the electrical parameter data information interferes with the delivery of therapy (i.e., stimulation is halted); and (2) the sampling rate is not high enough to allow fast change detection and adaptation.

There, thus, remains a need for an improved method and system for more efficiently sensing electrical parameter information while continuously providing stimulation therapy to tissue.

SUMMARY OF THE INVENTION

In accordance with a first aspect of the present inventions, a method of providing therapy to a patient implanted with an array of electrodes. The method comprises conveying a train of electrical stimulation pulses within a stimulation timing channel between a group of the electrodes to stimulate neural tissue (e.g., spinal cord tissue), thereby providing continuous therapy to the patient. The method further comprises sensing an electrical parameter (e.g., an electrical impedance, a field potential, and/or an evoked action potential) within a sensing timing channel using at least one of the electrodes. The method may further comprise transmitting sub-threshold pulses within the sensing timing channel between another group of the electrodes, wherein the electrical parameter is sensed in response to the transmission of the sub-threshold pulses.

In either event, the first stimulation timing channel and sensing timing channel are coordinated, such that the electrical parameter is sensed during the conveyance of the pulse train within time slots that do not temporally overlap any active phase of the stimulation pulses. For example, a hold-off period can be provided after the active phase of the stimulation pulses, such that no electrical parameter is sensed during the hold-off period.

One exemplary method further comprises conveying another train of electrical stimulation pulses within another stimulation timing channel between another group of the electrodes, thereby providing further continuous therapy to the patient. In this case, the stimulation timing channels and sensing timing channel are coordinated, such that the electrical parameter is sensed during the conveyance of the pulse trains within time slots that do not temporally overlap any active phase of the stimulation pulses. Furthermore, the stimulation timing channels may be coordinated, such that the stimulation pulses within the respective pulse trains do not temporally overlap any active phase of each other. The stimulation timing channels may be independently programmed with different stimulation parameters.

In accordance with a second aspect of the present inventions, a neurostimulation system is provided. The neurostimulation system comprises analog output circuitry configured for conveying a train of electrical stimulation pulses within a stimulation timing channel between a selected group of an array of electrodes to stimulate neural tissue in a manner that provides continuous therapy to the patient. The neurostimulation system further comprises monitoring circuitry configured for sensing electrical parameter (e.g., an electrical impedance, a field potential, and/or an evoked action potential) within a sensing timing channel using at least one of the electrodes. In one embodiment, the analog output circuitry is configured for transmitting sub-threshold pulses within the sensing timing channel between another group of electrodes, and the monitoring circuitry is configured for sensing the electrical parameter in response to the transmission of the sub-threshold pulses.

The neurostimulation system further comprises control circuitry configured for coordinating the first stimulation timing channel and sensing timing channel, such that the electrical parameter is sensed during the conveyance of the pulse train within time slots that do not temporally overlap any active phase of the stimulation pulses. The control circuitry may be configured for coordinating the first stimulation timing channel and sensing timing channel by providing a hold-off period after the active phase of the stimulation pulses, such that no electrical parameter is sensed during the hold-off period. The control circuitry may, e.g., take the form of a microcontroller or may take the form of circuitry, such as a digital state machine.

In one embodiment, the analog output circuitry is further configured for conveying another train of electrical stimulation pulses within another stimulation timing channel between another group of the electrodes in a manner that provides further continuous therapy to the patient, and the control circuitry is configured for coordinating the stimulation timing channels and sensing timing channel, such that the electrical parameter is sensed during the conveyance of the pulse trains within time slots that do not temporally overlap any active phase of the stimulation pulses. In this case, the control circuitry may be further configured for coordinating the stimulation timing channels, such that the stimulation pulses within the respective pulse trains do not temporally overlap any active phase of each other. The neurostimulation system may further comprise memory configured for storing different stimulation parameters for independently programming the stimulation timing channels. The neurostimulation system may further comprise telemetry circuitry configured wirelessly transmitting the sensed electrical parameter.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings.

Understanding that these drawings depict only typical embodiments of the invention and are not therefore to be considered limiting of its scope, the invention will be described and explained with additional specificity and detail through the use of the accompanying drawings in which:

FIG. 9 is a plot of the stimulation pulse trains and a sensed electrical parameter of FIG. 8 after arbitration has been performed to prevent overlap of the stimulation pulses and a sensed electrical parameter.

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
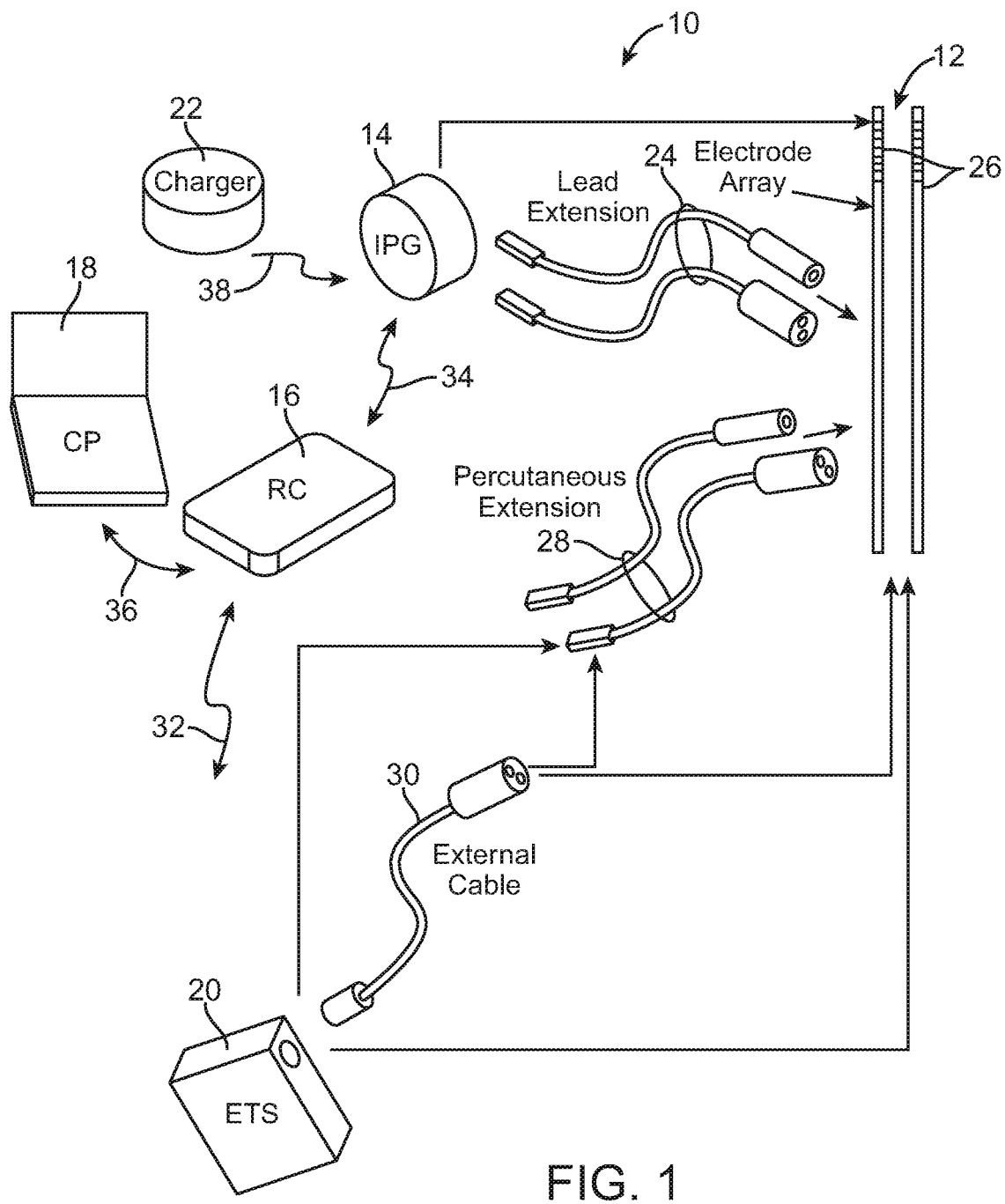
FIG. 1 is plan view of one embodiment of a spinal cord stimulation (SCS) system arranged in accordance with the present inventions.

Turning first to FIG. 1, an exemplary SCS system 10 generally includes one or more (in this case, two) implantable stimulation leads 12, an implantable pulse generator (IPG) 14, an external remote controller RC 16, a clinician's programmer (CP) 18, an External Trial Stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 are arranged in-line along the stimulation leads 12. In alternative embodiments, the electrodes 26 may be arranged in a two-dimensional pattern on a single paddle lead. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as that of the IPG 14, also delivers electrical stimulation energy in the form of a pulsed electrical waveform to the electrode array 26 in accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18). The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 2:
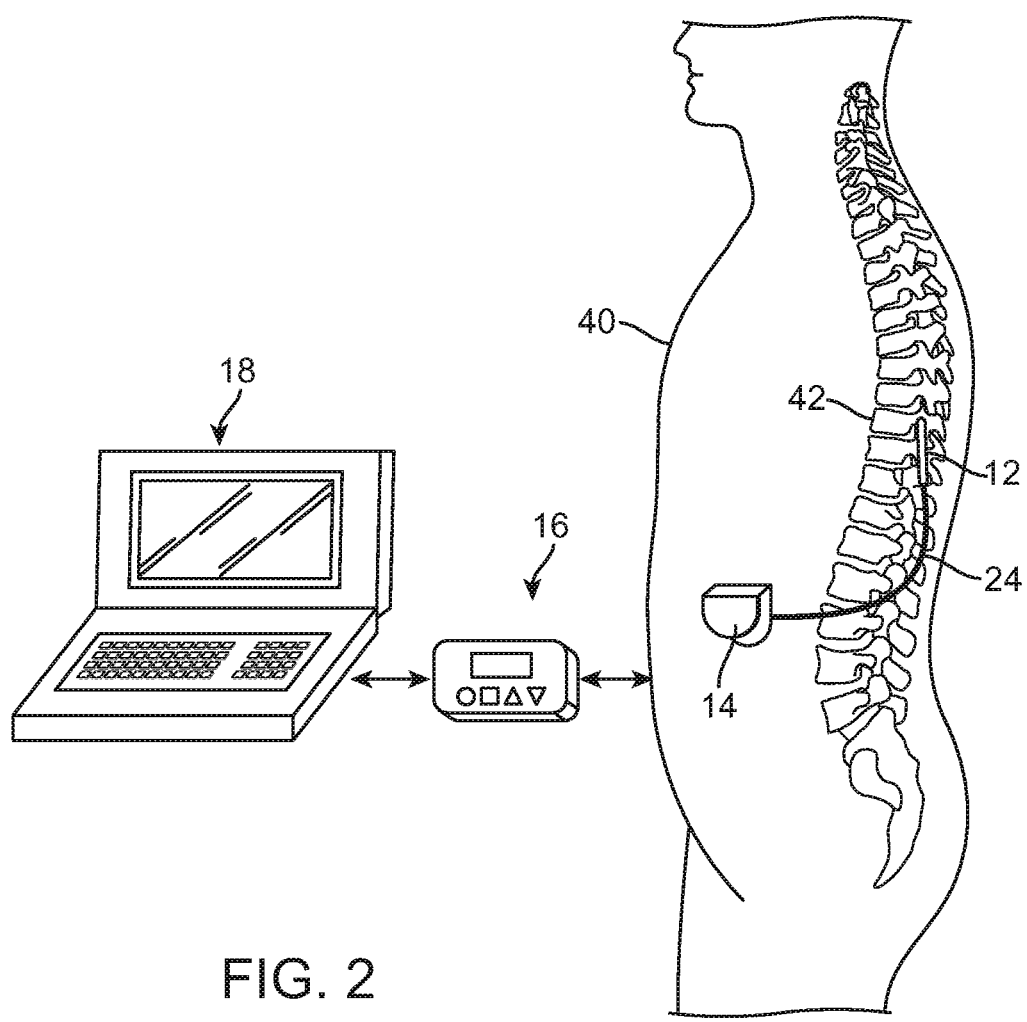
FIG. 2 is a plan view of the SCS system of FIG. 1 in use with a patient.

As shown in FIG. 2, the electrode leads 12 are implanted within the spinal column 42 of a patient 40. The preferred placement of the electrode leads 12 is adjacent, i.e., resting upon, the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the electrode leads 12. As there shown, the CP 18 communicates with the IPG 14 via the RC 16.

Figure 3:
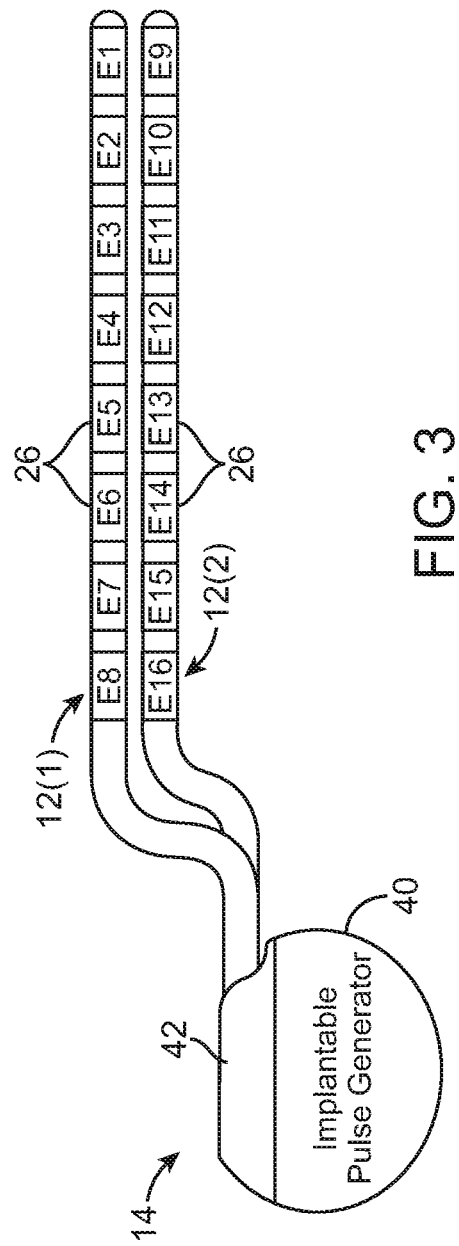
FIG. 3 is a profile view of an implantable pulse generator (IPG) used in the SCS system of FIG. 1.

Referring now to FIG. 3, the external features of the stimulation leads 12 and the IPG 14 will be briefly described. One of the stimulation leads 12(1) has eight electrodes 26 (labeled E1-E8), and the other stimulation lead 12(2) has eight electrodes 26 (labeled E9-E16). The actual number and shape of leads and electrodes will, of course, vary according to the intended application. The IPG 14 comprises an outer case 40 for housing the electronic and other components (described in further detail below), and a connector 42 to which the proximal ends of the stimulation leads 12(1) and 12(2) mate in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

As will be described in further detail below, the IPG 14 includes pulse generation circuitry that provides electrical conditioning and stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

Figure 4:
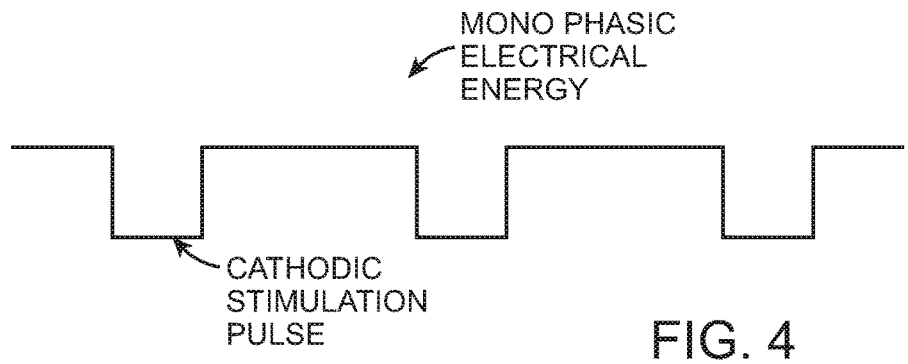
FIG. 4 is a plot of mono-phasic cathodic electrical stimulation energy.

The stimulation energy may be delivered between a specified group of electrodes as monophasic electrical energy or multiphasic electrical energy. As illustrated in FIG. 4, monophasic electrical energy includes a series of pulses that are either all negative (cathodic), or alternatively all positive (anodic). Multiphasic electrical energy includes a series of pulses that alternate between positive and negative.

Figure 5A:
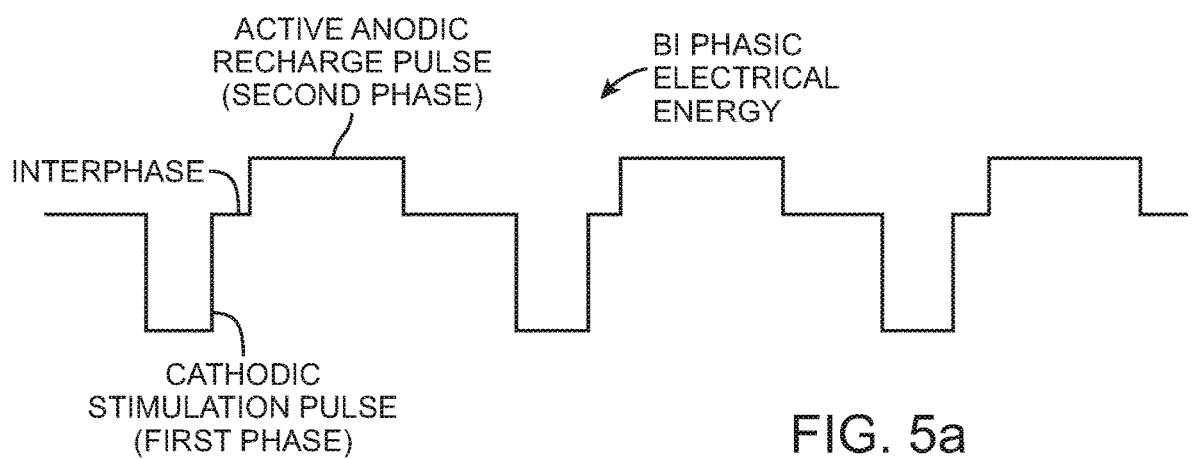
FIG. 5a is a plot of bi-phasic electrical stimulation energy having a cathodic stimulation pulse and an active recharge pulse.
Figure 5B:
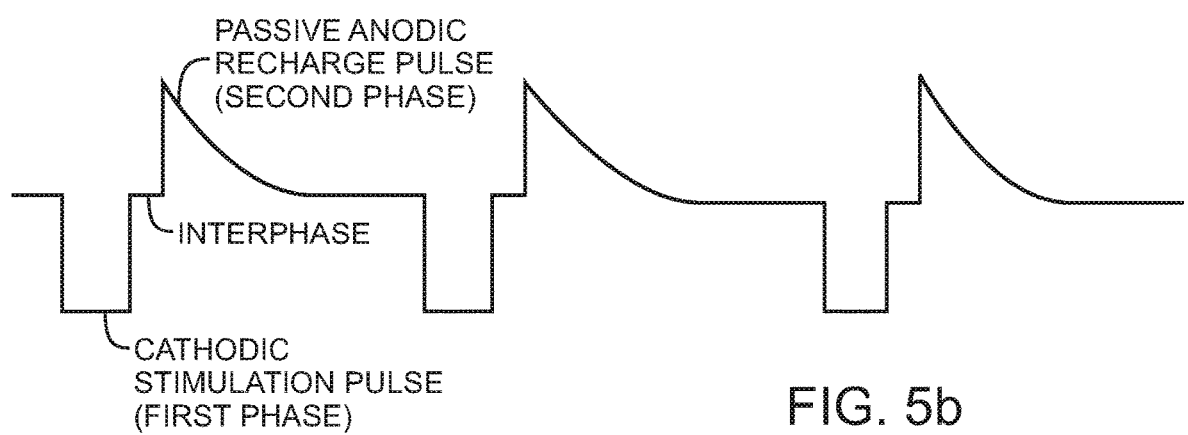
FIG. 5b is a plot of bi-phasic electrical stimulation energy having a cathodic stimulation pulse and a passive recharge pulse.

For example, as illustrated in FIGS. 5a and 5b, multiphasic electrical energy may include a series of biphasic pulses, with each biphasic pulse including a cathodic (negative) stimulation pulse (during a first phase) and an anodic (positive) recharge pulse (during a second phase) that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

The second phase may have an active recharge pulse (FIG. 5a), wherein electrical current is actively conveyed through the electrode via current or voltage sources, and a passive recharge pulse, or the second phase may have a passive recharge pulse (FIG. 5b), wherein electrical current is passively conveyed through the electrode via redistribution of the charge flowing from coupling capacitances present in the circuit. Using active recharge, as opposed to passive recharge, allows faster recharge, while avoiding the charge imbalance that could otherwise occur. Another electrical pulse parameter in the form of an interphase can define the time period between the pulses of the biphasic pulse (measured in microseconds).

Figure 6:
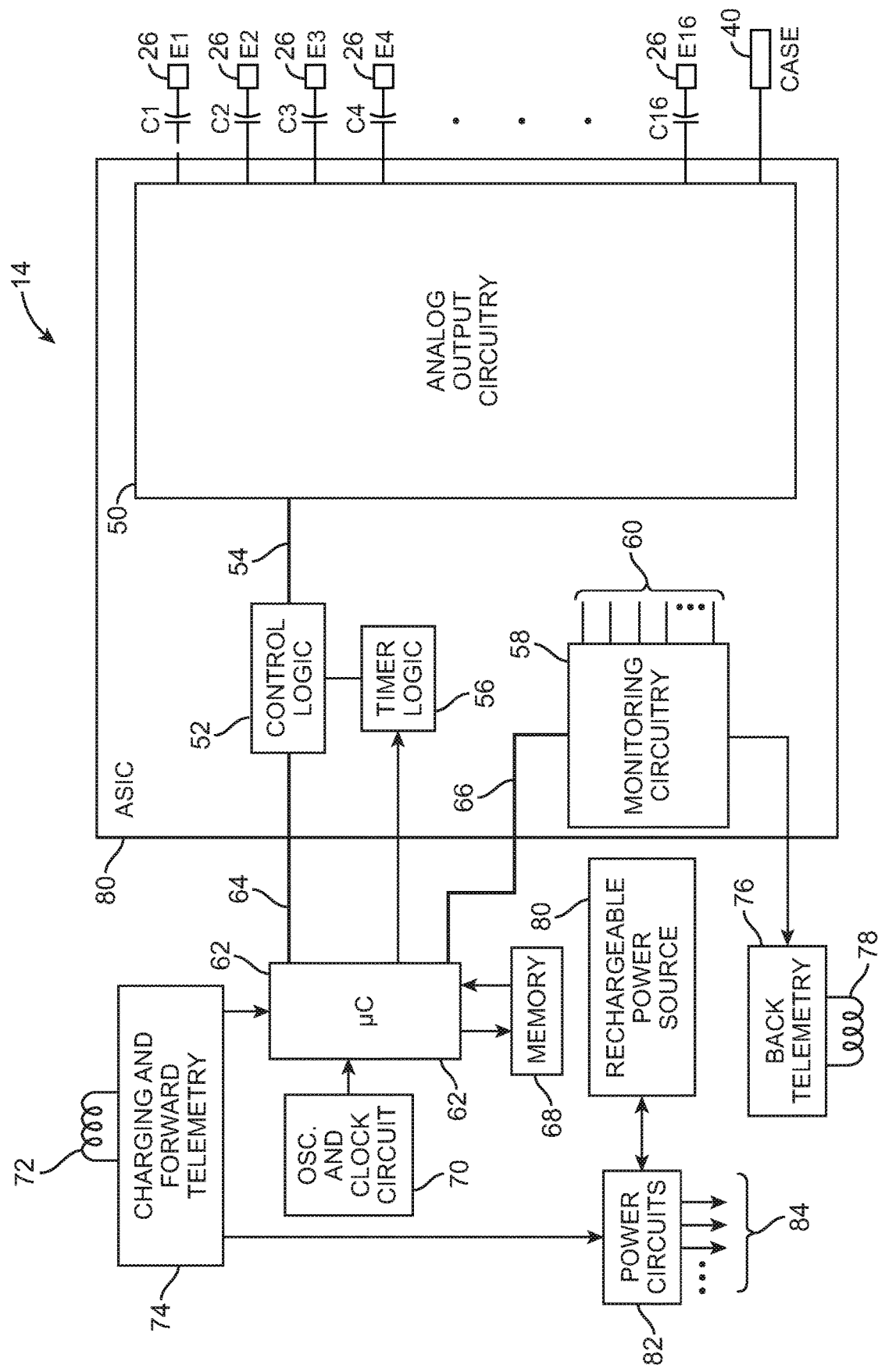
FIG. 6 is a block diagram of the internal components of the IPG of FIG. 3.

Turning next to FIG. 6, the main internal components of the IPG 14 will now be described. The IPG 14 includes analog output circuitry 50 capable of individually generating electrical stimulation pulses via capacitors C 1-C 16 at the electrodes 26 (E1-E16) of specified amplitude under control of control logic 52 over data bus 54. The duration of the electrical stimulation (i.e., the width of the stimulation pulses), is controlled by the timer logic circuitry 56. The analog output circuitry 50 may either comprise independently controlled current sources for providing stimulation pulses of a specified and known amperage to or from the electrodes 26, or independently controlled voltage sources for providing stimulation pulses of a specified and known voltage at the electrodes 26.

Any of the N electrodes may be assigned to up to k possible groups or "channels." In one embodiment, k may equal four. The channel identifies which electrodes are selected to synchronously source or sink current to create an electric field in the tissue to be stimulated. Amplitudes and polarities of electrodes on a channel may vary, e.g., as controlled by the RC 16. External programming software in the CP 18 is typically used to set stimulation parameters including electrode polarity, amplitude, pulse rate and pulse width for the electrodes of a given channel, among other possible programmable features.

The N programmable electrodes can be programmed to have a positive (sourcing current), negative (sinking current), or off (no current) polarity in any of the k channels. Moreover, each of the N electrodes can operate in a bipolar mode or multipolar mode, e.g., where two or more electrode contacts are grouped to source/sink current at the same time. Alternatively, each of the N electrodes can operate in a monopolar mode where, e.g., the electrode contacts associated with a channel are configured as cathodes (negative), and the case electrode (i.e., the IPG case) is configured as an anode (positive).

Further, the amplitude of the current pulse being sourced or sunk to or from a given electrode may be programmed to one of several discrete current levels, e.g., between 0 to 10 mA in steps of 0.1 mA. Also, the pulse width of the current pulses is preferably adjustable in convenient increments, e.g., from 0 to 1 milliseconds (ms) in increments of 10 microseconds (µs). Similarly, the pulse rate is preferably adjustable within acceptable limits, e.g., from 0 to 1000 pulses per second (pps). Other programmable features can include slow start/end ramping, burst stimulation cycling (on for X time, off for Y time), interphase, and open or closed loop sensing modes.

The operation of this analog output circuitry 50, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 further comprises monitoring circuitry 58 for monitoring the status of various nodes or other points 60 throughout the IPG 14, e.g., power supply voltages, temperature, battery voltage, and the like. The monitoring circuitry 58 is also configured for measuring physiological data, which may be used in a closed-loop or open-loop fashion with the tissue stimulation function.

For example, the impedance between the respective electrodes 26 and the IPG case 40 can be measured. Notably, the electrodes 26 fit snugly within the epidural space of the spinal column, and because the tissue is conductive, there is an impedance associated therewith that indicates how easily current flows therethrough. Because implanted electrical stimulation systems depend upon the stability of the devices to be able to convey electrical stimulation pulses of known energy to the target tissue to be excited, measuring electrode impedance is important in order to determine the coupling efficiency between the respective electrode 26 and the tissue.

For example, if the electrode impedance is too high, the respective electrode 26 may be inefficiently coupled to the tissue that it is to stimulate. As a result, an excessive amount of compliance voltage may need to be generated in order to effectively supply stimulation energy to the electrode 26 if the analog output circuitry 50 uses current-controlled sources, thereby resulting in an inefficient use of the battery power, or the stimulation energy supplied to the electrode 26 may be otherwise inadequate if the analog output circuitry 50 uses voltage-controlled sources. Other electrical parameter data, such as field potential and evoked action potential, may also be measured to determine the coupling efficiency between the electrodes 26 and the tissue.

Measurement of the electrode impedance also facilitates fault detection with respect to the connection between the electrodes 26 and the analog output circuitry 50 of the IPG 14. For example, if the impedance is too high, that suggests the connector 42 and/or leads 12 may be open or broken. If the impedance is too low, that suggests that there may be a short circuit somewhere in the connector 42 and/or leads 12. In either event (too high or too low impedance), the IPG 14 may be unable to perform its intended function.

The impedance measurement technique may be performed by measuring impedance vectors, which can be defined as impedance values measured between selected pairs of electrodes 26. The interelectrode impedance may be determined in various ways. For example, a known current (in the case where the analog output circuitry 50 is sourcing current) can be applied between a pair of electrodes 26, a voltage between the electrodes 26 can be measured, and an impedance between the electrodes 26 can be calculated as a ratio of the measured voltage to known current. Or a known voltage (in the case where the analog output circuitry 50 is sourcing voltage) can be applied between a pair of electrodes 26, a current between the electrodes 26 can be measured, and an impedance between the electrodes 26 can be calculated as a ratio of the known voltage to measured current.

The field potential measurement technique may be performed by generating an electrical field at selected ones of the electrodes 26 and recording the electrical field at other selected ones of the lead electrodes 26. This may be accomplished in one of a variety of manners. For example, an electrical field may be generated conveying electrical energy to a selected one of the electrodes 26 and returning the electrical energy at the IPG case 40. Alternatively, multipolar configurations (e.g., bipolar or tripolar) may be created between the lead electrodes 26. Or, an electrode that is sutured (or otherwise permanently or temporarily attached (e.g., an adhesive or gel-based electrode) anywhere on the patient's body may be used in place of the case IPG outer case 40 or lead electrodes 26. In either case, while a selected one of the electrodes 26 is activated to generate the electrical field, a selected one of the electrodes 26 (different from the activated electrode) is operated to record the voltage potential of the electrical field.

The evoked potential measurement technique may be performed by generating an electrical field at one of the electrodes 26, which is strong enough to depolarize (or "stimulate") the neurons adjacent the stimulating electrode beyond a threshold level, thereby inducing the firing of action potentials (APs) that propagate along the neural fibers. Such stimulation is preferably supra-threshold, but not uncomfortable. A suitable stimulation pulse for this purpose is, for example, 4 mA for 200 µS. While a selected one of the electrodes 26 is activated to generate the electrical field, a selected one or ones of the electrodes 26 (different from the activated electrode) is operated to record a measurable deviation in the voltage caused by the evoked potential due to the stimulation pulse at the stimulating electrode.

Further details discussing the measurement of electrical parameter data, such as electrode impedance, field potential, and evoked action potentials, as well as other parameter data, such as pressure, translucence, reflectance and pH (which can alternatively be used), to determine the coupling efficiency between an electrode and tissue are set forth in U.S. patent application Ser. No. 10/364,436, entitled "Neural Stimulation System Providing Auto Adjustment of Stimulus Output as a Function of Sensed Impedance," U.S. patent application Ser. No. 10/364,434, entitled "Neural Stimulation System Providing Auto Adjustment of Stimulus Output as a Function of Sensed Pressure Changes," U.S. Pat. No. 6,993,384, entitled "Apparatus and Method for Determining the Relative Position and Orientation of Neurostimulation Leads," and U.S. patent application Ser. No. 11/096,483, entitled "Apparatus and Methods for Detecting Migration of Neurostimulation Leads," which are expressly incorporated herein by reference.

The IPG 14 further comprises processing circuitry in the form of a microcontroller (µC) 62 that controls the control logic over data bus 64, and obtains status data from the monitoring circuitry 58 via data bus 66. The IPG 14 additionally controls the timer logic 56. The IPG 14 further comprises memory 68 and oscillator and clock circuitry 70 coupled to the microcontroller 62. The microcontroller 62, in combination with the memory 68 and oscillator and clock circuit 70, thus comprise a microprocessor system that carries out a program function in accordance with a suitable program stored in the memory 68. Alternatively, for some applications, the function provided by the microprocessor system may be carried out by a suitable state machine.

Thus, the microcontroller 62 generates the necessary control and status signals, which allow the microcontroller 62 to control the operation of the IPG 14 in accordance with a selected operating program and stimulation parameters. In controlling the operation of the IPG 14, the microcontroller 62 is able to individually generate a train of stimulus pulses at the electrodes 26 using the analog output circuitry 60, in combination with the control logic 52 and timer logic 56, thereby allowing each electrode 26 to be paired or grouped with other electrodes 26, including the monopolar case electrode. In accordance with stimulation parameters stored within the memory 68, the microcontroller 62 may control the polarity, amplitude, rate, pulse width and channel through which the current stimulus pulses are provided. The microcontroller 62 also facilitates the storage of electrical parameter data (or other parameter data) measured by the monitoring circuitry 58 within memory 68, and also provides any computational capability needed to analyze the raw electrical parameter data obtained from the monitoring circuitry 58 and compute numerical values from such raw electrical parameter data.

Significantly, as will be described in further detail below, the microcontroller 62 uses a set of arbitration rules to control the monitoring circuitry 58 to sense an electrical parameter within one of the channels k (effectively making it a sensing channel) that is not occupied by the stimulation pulses. Alternatively, functions such as the management of stimulation pulses, timing information, and channel arbitration may be performed in a digital state machine, with the microcontroller 62 having a supervisory role to manage information flow, e.g., sending stimulation parameters to the analog circuitry and/or converting sampled analog data into a digital form, and then post-processing the digital data for storage or transmission to the RC 16.

The IPG 14 further comprises an alternating current (AC) receiving coil 72 for receiving programming data (e.g., the operating program and/or stimulation parameters) from the RC 16 (shown in FIG. 1) in an appropriate modulated carrier signal, and charging and forward telemetry circuitry 74 for demodulating the carrier signal it receives through the AC receiving coil 72 to recover the programming data, which programming data is then stored within the memory 68, or within other memory elements (not shown) distributed throughout the IPG 14.

The IPG 14 further comprises back telemetry circuitry 76 and an alternating current (AC) transmission coil 78 for sending informational data sensed through the monitoring circuitry 58 to the RC 16. The back telemetry features of the IPG 14 also allow its status to be checked. For example, when the RC 16 initiates a programming session with the IPG 14, the capacity of the battery is telemetered, so that the external programmer can calculate the estimated time to recharge. Any changes made to the current stimulus parameters are confirmed through back telemetry, thereby assuring that such changes have been correctly received and implemented within the implant system. Moreover, upon interrogation by the RC 16, all programmable settings stored within the IPG 14 may be uploaded to the RC 16. Significantly, the back telemetry features allow raw or processed electrical parameter data (or other parameter data) previously stored in the memory 68 to be downloaded from the IPG 14 to the RC 16, which information can be used to track the physical activity of the patient.

The IPG 14 further comprises a rechargeable power source 80 and power circuits 82 for providing the operating power to the IPG 14. The rechargeable power source 80 may, e.g., comprise a lithium-ion or lithium-ion polymer battery. The rechargeable battery 80 provides an unregulated voltage to the power circuits 82. The power circuits 82, in turn, generate the various voltages 84, some of which are regulated and some of which are not, as needed by the various circuits located within the IPG 14. The rechargeable power source 80 is recharged using rectified AC power (or DC power converted from AC power through other means, e.g., efficient AC-to-DC converter circuits, also known as "inverter circuits") received by the AC receiving coil 72. To recharge the power source 80, an external charger (not shown), which generates the AC magnetic field, is placed against, or otherwise adjacent, to the patient's skin over the implanted IPG 14. The AC magnetic field emitted by the external charger induces AC currents in the AC receiving coil 72. The charging and forward telemetry circuitry 74 rectifies the AC current to produce DC current, which is used to charge the power source 80. While the AC receiving coil 72 is described as being used for both wirelessly receiving communications (e.g., programming and control data) and charging energy from the external device, it should be appreciated that the AC receiving coil 72 can be arranged as a dedicated charging coil, while another coil, such as coil 78, can be used for bi-directional telemetry.

It should be noted that the diagram of FIG. 6 is functional only, and is not intended to be limiting. Those of skill in the art, given the descriptions presented herein, should be able to readily fashion numerous types of IPG circuits, or equivalent circuits, that carry out the functions indicated and described, which functions include not only producing a stimulus current or voltage on selected groups of electrodes, but also the ability to measure electrical parameter data at an activated or non-activated electrode.

Additional details concerning the above-described and other LPGs may be found in U.S. Pat. No. 6,516,227, U.S. Patent Publication No. 2003/0139781, now issued as U.S. Pat. No. 6,993,384, and U.S. patent application Ser. No. 11/138,632, now issued as U.S. Pat. No. 7,539,538, entitled "Low Power Loss Current Digital-to-Analog Converter Used in an Implantable Pulse Generator," which are expressly incorporated herein by reference. It should be noted that rather than an IPG, the SCS system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 7:
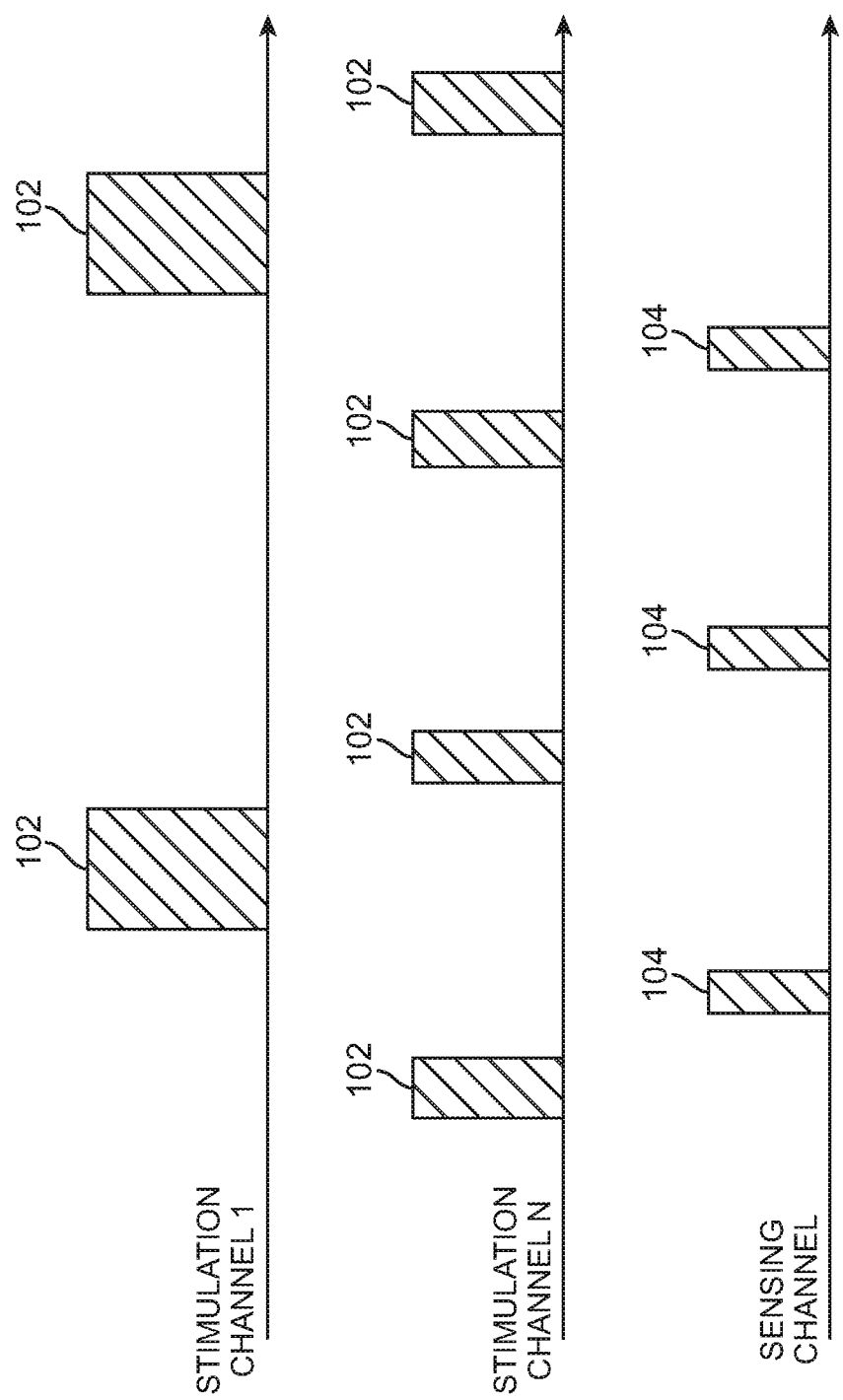
FIG. 7 is a plot of stimulation pulses that are transmitted in an N number of stimulation timing channels, and a sensed electrical parameter measured within a sensing timing channel.

As briefly discussed above, the microcontroller 62 (or alternatively, a digital state machine), using a set of arbitration rules, controls the monitoring circuitry 58 to sense the electrical parameter within a sensing channel that is not occupied by the stimulation pulses. That is, not only is the control circuitry configured for coordinating the stimulation timing channels, such that the stimulation pulses within the respective pulse trains do not temporally overlap any active phase of each other, the microcontroller 62 is configured for coordinating the stimulation timing channels and sensing timing channel, such that electrical parameter is sensed within time slots that do not temporally overlap any active phase of the stimulation pulses. For example, with reference to FIG. 7, stimulation pulses 102 are shown as being transmitted in stimulation channels 1, . . . N, while the electrical parameter 104 is shown as being sensed within the sensing channel during time slots that are not occupied by the stimulation pulses 102.

If the analog output circuitry 50 transmits pulses for the sensing function (e.g., when measuring impedance, field potentials, or evoked action potentials), these pulses are preferably transmitted within the sensing timing channel between a selected group of electrodes 26, in which case, the monitoring circuitry 58 senses the electrical parameter in response to the transmission of the pulses. In some cases, e.g., when measuring impedance and field potentials, the pulses used in the sensing function have relatively low charge-requirements (i.e., sub-threshold pulses) to lessen the chances of patient perception during the sensing function. Also, as can be easily understood, the faster the sensing measurements are performed, the lower the probability that the measurements will temporally overlap the stimulation pulses. With this in mind, the monitoring circuitry 58 should be able to allow a fast sampling rate and require minimal charge injection during the sensing pulse, while still ensuring acceptable Signal-to-Noise ratio of the measurement.

Figure 8:
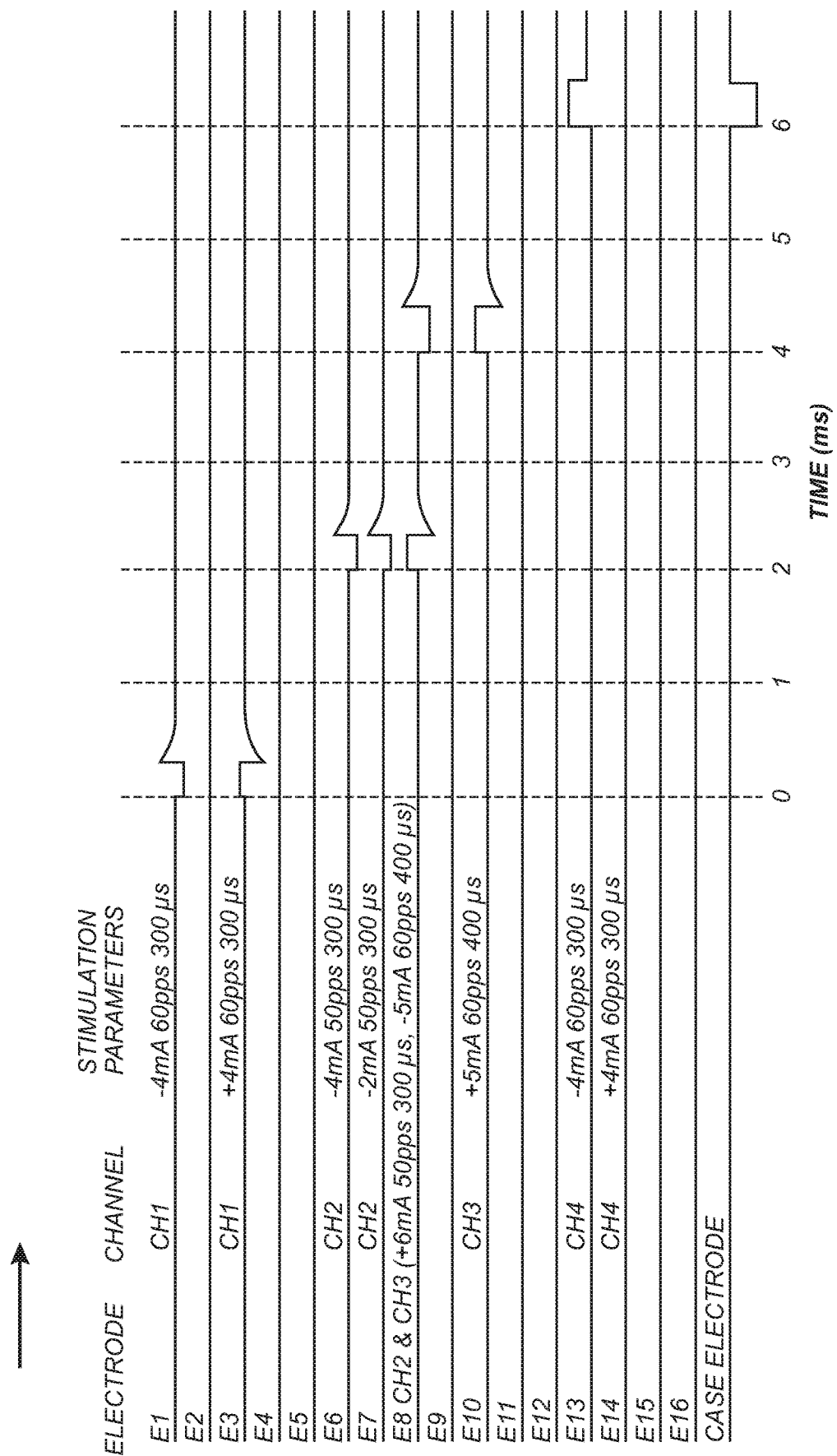
FIG. 8 is a plot of stimulation pulse trains transmitted within Timing Channels 1-3 and a sensed electrical parameter measured within Timing Channel 4.

Referring to FIG. 8, one example of a technique for preventing the stimulation pulses transmitted respectively in two stimulation timing channels and the sensing of the electrical parameter in the sensing timing channel from overlapping each other will now be described. The horizontal axis is time, divided by increments of 1 millisecond (ms), while the vertical axis represents the amplitude of the electrical current pulse, if any, applied to one of the sixteen electrodes E1-E16.

As there shown, a first train of bi-phasic stimulation pulses 110 (only one shown) is transmitted in Timing Channel 1, a second train of bi-phasic stimulation pulses 112 (only one shown) is transmitted in Timing Channel 2, a third train of bi-phasic stimulation pulses 114 (only one shown) is transmitted in Timing Channel 3, and a train of physiological samples 116 (only one shown) are taken in Timing Channel 4. Each of the bi-phasic stimulation pulses includes an active stimulation phase (first phase) 118, a recharge phase (second phase) 120, and an interphase (not shown) between the stimulation and recharge phases.

In the example, the initial stimulation pulse 110 is represented by a 4 mA pulse transmitted between electrode E1 and electrode E3 within Timing Channel 1 at t=0 ms, with a cathodic (negative) current pulse of −4 mA appearing on electrode E1 and an anodic (positive) current pulse of +4 mA appearing on electrode E3. Additionally, other stimulation parameters associated with the bi-phasic stimulation pulse 110 are shown as being set at a rate of 60 pulses per second (pps), and a pulse width of 300 microseconds (μs).

The initial stimulation pulse 112 is represented by a 6 mA pulse transmitted between electrodes E6, E7 and electrode E8 within Timing Channel 2 at t=2 ms, with cathodic (negative) current pulses of −4 mA and −2 mA appearing respectively on electrodes E6, E7, and an anodic (positive) current pulse of +6 mA appearing on electrode E8. Additionally, other stimulation parameters associated with the bi-phasic stimulation pulse 112 are shown as being set at a rate of 50 pulses per second (pps), and a pulse width of 300 microseconds (μs).

The initial stimulation pulse 114 is represented by a 5 mA pulse transmitted between electrode E8 and electrode E10 within Timing Channel 3 at t=4 ms, with a cathodic (negative) current pulse of −5 mA appearing on electrode E8 and an anodic (positive) current pulse of +5 mA appearing on electrode E10. Additionally, other stimulation parameters associated with the bi-phasic stimulation pulse 114 are shown as being set at a rate of 60 pulses per second (pps), and a pulse width of 400 microseconds (μs).

The initial sample 116 is shown as being taken at electrode E13 and referenced at the IPG case at t=6 ms.

The particular electrodes that are used with each of the four timing channels illustrated in FIG. 8 are only exemplary of many different combinations of electrode paring and electrode sharing that could be used. That is, any of the timing channels may be programmed to connect to any grouping of the electrodes, including the IPG case. While it is typical that only two electrodes be paired together for use by a given channel, as is the case with Timing Channels 1, 3, and 4 shown in FIG. 8, it is to be noted that any number of electrodes may be grouped and used by a given timing channel. When more than two electrodes are used with a given channel, the sum of the current sourced from the anodic (positive) electrodes should be equal to the current sunk into the cathodic (negative) electrodes, as is the case with Timing Channel 2 shown in FIG. 8.

The microcontroller 62 arbitrates the timing channels in accordance with the following principles. Once a non-overlapping timing channel begins a stimulation (or sample) pulse, the start of the pulses (or samples) from any other overlapping timing channel is delayed until the ongoing first phase of the pulse is completed and a hold-off period has been completed. If the start of two or more non-overlapping timing channels are delayed by an ongoing pulse and hold-off period, the pending timing channels are started in the order they would have occurred without arbitration. If two non-overlapping timing channels are scheduled to start simultaneously, the lower number channel takes priority and starts first (i.e., Timing Channel 1 before Timing Channel 2, Timing Channel 2 before Timing Channel 3, and Timing Channel 3 before Timing Channel 4). Because the sensing function is associated with Timing Channel 4 in this example, the sensing function has the lowest priority.

Current from any stimulus pulse (first phase) or active recharge (active second phase) is prevented from passing through any electrode undergoing passive recharge. The delivery of an active first phase or active second phase on any electrode takes precedence over all ongoing passive recharge phases. Electrodes undergoing passive recharge have their passive recharge phases temporarily interrupted during the active phase(s). If the electrode is not part of the active phase, it remains in a high impedance state (i.e., turned OFF) until the active phase is completed.

The above arbitration principles are illustrated in FIG. 9, which shows the stimulation pulses and sample pulses associated with active electrodes. Recognizing that a channel comprises those electrodes that provide a stimulus current or measured sample of the same pulse width at the same time, Timing Channel 1 comprises the group of electrodes E1, E3; Timing Channel 2 comprises the group of electrodes E6, E7, E8; Timing Channel 3 comprises the group of electrodes E8, E10; and Timing Channel 4 comprises the group of electrodes E9, IPG case. As shown in FIG. 8, the normal timing of the channel firings, without arbitration, would be as follows: Timing Channel 1 firing at time T1, Timing Channel 2 firing at time T2, Timing Channel 3 firing at time T3, and Timing Channel 4 firing at time T4.

With arbitration, however, the timing of the channel firings is shown in FIG. 9. The first phase period 120 of Timing Channel 1 begins at time T1. After the first phase period 120 is completed, the interphase period 122 and hold-off period 126 of Timing Channel 1 begin, and after completion of the interphase period 122, the second phase period 124 begins. The second phase period 124 may be a fixed period of 5 ms, and the hold-off period 126 may be a programmable delay, ranging from 1 ms to 64 ms (in the illustrated embodiment, the hold-off period 126 is about 3 ms). During the hold-off period 126, no other timing channel will be active (i.e., will not stimulate or sense). Thus, at time T2, when Timing Channel 2 would normally fire, it is prevented from firing. Rather, Timing Channel 2 must wait a time period 126 until the hold-off period 124 concludes.

At the conclusion of the hold-off period 126, the first phase period 130 of Timing Channel 2, which has priority over Timing Channel 3, begins. At this time, which is still during the second phase period 124 of Timing Channel 1, the passive recharge taking place in Timing Channel 1 is interrupted temporarily (e.g., for the duration of the active first phase period 130 of Timing Channel 2). After the first phase period 130 is completed, the interphase period 132 and hold-off period 136 of Timing Channel 2 begin, and after completion of the interphase period 132, the second phase period 134 begins. The second phase period 134 may be a fixed period of 5 ms, and the hold-off period 136 is programmed to be 15 ms. Neither Timing Channel 3 nor Timing Channel 4 is allowed to fire during the hold-off period 136.

As soon as the hold-off period 136 for Timing Channel 2 concludes, Timing Channels 3 and 4 are both past due for firing. The first phase period 140 of Timing Channel 3, which has priority over Timing Channel 4, begins. After the first phase period 140 is completed, the interphase period 142 and hold-off period 146 of Timing Channel 3 begins, and after completion of the interphase period 142, the second phase period 144 of Timing Channel 3 begins. The second phase period 144 may be a fixed period of 5 ms, and the hold-off period 146 is programmed to be 3 ms. Timing Channel 4 is not allowed to fire during the hold-off period 146.

As soon as the hold-off period 146 for Timing Channel 3 concludes, Timing Channel 4 is past due for firing. The sensing period 150 of Timing Channel 4 begins. At this time, which is still during the second phase period 144 of Timing Channel 3, the passive recharge taking place in Timing Channel 3 is interrupted temporarily (e.g., for the duration of the active first phase period 140 of Timing Channel 3). Alternatively, the beginning of the sensing period 150 can be delayed until the second phase period 144 of Timing Channel 3 has been completed. After the sensing period 150 is completed, the hold-off period 156 of Timing Channel 4 begins. The hold-off period 156 is programmed to be 3 ms. Timing Channel 1 is not allowed to fire during the hold-off period 156. As soon as the hold-off period 156 for Timing Channel 4 concludes, the first phase period 120 of Timing Channel 1 begins, and the process repeats itself.

It should be noted that although the arbitration methodology has been described as preventing any overlap between the stimulation and sensing channels, there may be some applications in which partial overlap between the stimulation and sensing channels can be tolerated, and in fact, preferred. For example, in Neural Response Imaging involving the measurement of evoked potentials using cochlear implants, the stimulation and sensing channels may overlap as long as they are synchronized with a certain delay. It can be appreciated that the same concept of timing management between the stimulation and the sensing activities applies in this case. The key goal of the arbitration methodology is to ensure therapy is not modified by the sensing, whether this requires no-overlapping between the stimulation and sensing channels (necessary for impedance or field potential measurements) or other forms of sensing where the timing relationship between the stimulation and sensing channels may be different.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neurostimulation system configured for use to deliver a closed-loop continuous therapy during a time period using a sensed electrical parameter as feedback for the closed-loop continuous therapy to maintain a desired target for the sensed electrical parameter, comprising:
  a pulse generator configured to deliver electrical stimulation pulses, according to a set of stimulation parameters, for the closed-loop continuous therapy, wherein the closed-loop continuous therapy affects the sensed electrical parameter;
  a sensor configured to sense the electrical parameter using at least one electrode; and
  a controller configured to:
    control timing for the pulse generator to deliver the electrical stimulation pulses for the closed-loop continuous therapy throughout the time period;
    coordinate timing for the sensor to sense the electrical parameter, without modifying the timing for the pulse generator to deliver the electrical stimulation pulses for the closed-loop continuous therapy, by sensing the electrical parameter during times within the time period that do not temporally overlap with the electrical stimulation pulses; and
    provide closed-loop stimulation control to maintain the desired target for the sensed electrical parameter throughout the time period by updating the set of stimulation parameters using the sensed electrical parameter.

2. The neurostimulation system of claim 1, wherein the controller is configured to coordinate timing by preventing the electrical stimulation pulses and the sensing from providing overlapping pulses.

3. The neurostimulation system of claim 1, wherein the controller is configured to coordinate timing by allowing the stimulation and sensing channels to have overlapping pulses only when the sensing channel is synchronized to the stimulation channel with a delay.

4. The neurostimulation system of claim 1, wherein the electrical parameter includes an evoked action potential.

5. The neurostimulation system of claim 1, wherein the electrical parameter includes an electrical impedance or a field potential.

6. The neurostimulation system of claim 1, wherein the controller is configured to coordinate timing by controlling the pulse generator to generate a pulse for use in sensing and controlling the sensor to sense the electrical parameter in response to the generated pulse for use in sensing.

7. The neurostimulation system of claim 6, wherein the controller is configured to prevent the generated pulse for use in sensing from overlapping with the electrical stimulation pulses of the continuous therapy.

8. The neurostimulation system of claim 1, wherein the pulse generator is configured to deliver electrical stimulation pulses with active recharge pulses, and the controller is configured to coordinate timing to prevent the sensing of the electrical parameter from overlapping the active recharge pulses.

9. The neurostimulation system of claim 1, wherein the controller is configured to delay the sensing of the electrical parameter until a hold-off period has elapsed following the electrical stimulation pulses.

10. The neurostimulation system of claim 1, wherein the electrical stimulation is delivered on a first channel and the electrical parameter is sensed on a second channel.

11. A method of using a neurostimulation system and electrodes to provide closed-loop continuous therapy to a patient during a time period where closed-loop stimulation control uses a sensed electrical parameter as feedback for the closed-loop continuous therapy to maintain a desired target for the sensed electrical parameter, wherein the neurostimulation system has a pulse generator for generating electrical stimulation pulses, a sensor for sensing the electrical parameter, and a controller, wherein the method comprises:
  delivering, using the pulse generator, electrical stimulation pulses according to a set of stimulation parameters to at least one of the electrodes to stimulate neural tissue for the closed-loop continuous therapy to the patient, wherein the closed-loop continuous therapy affects the sensed electrical parameter;
  controlling timing, using the controller, for the pulse generator to deliver the electrical stimulation pulses for the closed-loop continuous therapy throughout the time period;
  sensing the electrical parameter using the sensor including at least one of the electrodes;
  coordinating, using the controller, timing for the sensor to sense the electrical parameter, without modifying the timing for the pulse generator to deliver the electrical stimulation pulses for the closed-loop continuous therapy, by sensing the electrical parameter during times within the time period that do not temporally overlap with the electrical stimulation pulses; and
  providing closed-loop stimulation control to maintain the desired target for the sensed electrical parameter throughout the time period by updating the set of stimulation parameters using the controller and the sensed electrical parameter.

12. The method of claim 11, wherein the controller is configured to coordinate timing by preventing the electrical stimulation pulses and the sensing from providing overlapping pulses.

13. The method of claim 11, wherein the controller is configured to coordinate timing by allowing stimulation and sensing channels to have overlapping pulses only when the sensing channel is synchronized to the stimulation channel with a delay.

14. The method of claim 11, wherein the electrical parameter includes an evoked action potential.

15. The method of claim 11, wherein the electrical parameter includes an electrical impedance or a field potential.

16. A non-transitory machine-readable medium including instructions, which when executed by a machine, cause the machine to implement a method that uses electrodes to provide closed-loop continuous therapy during a time period to a patient where closed-loop stimulation control uses a sensed electrical parameter as feedback for the closed-loop continuous therapy to maintain a desired target for the sensed electrical parameter, the method comprising:
  delivering, using a pulse generator, electrical stimulation pulses according to a set of stimulation parameters to at least one of the electrodes to stimulate neural tissue for the closed-loop continuous therapy to the patient, wherein the closed-loop continuous therapy affects the sensed electrical parameter;
  controlling timing, using a controller, for the pulse generator to deliver the electrical stimulation pulses for the closed-loop continuous therapy throughout the time period;
  sensing the electrical parameter using the sensor including at least one of the electrodes;
  coordinating, using the controller, timing for the sensor to sense the electrical parameter, without modifying the timing for the pulse generator to deliver the electrical stimulation pulses for the closed-loop continuous therapy, by sensing the electrical parameter during times within the time period that do not temporally overlap with the electrical stimulation pulses; and providing closed-loop stimulation control to maintain the desired target for the sensed electrical parameter throughout the time period by updating the set of stimulation parameters using the controller and using the sensed electrical parameter.

17. The non-transitory machine-readable medium of claim 16, wherein the method further comprises controlling the pulse generator to generate a pulse for use in sensing and controlling the sensor to sense the electrical parameter in response to the generated pulse for use in sensing.

18. The non-transitory machine-readable medium of claim 17, wherein the generated pulse for use in sensing is prevented from overlapping with the electrical stimulation pulses of the continuous therapy.

19. The non-transitory machine-readable medium of claim 16, wherein the delivering electrical stimulation pulses includes delivering electrical stimulation pulses with active recharge pulses, and the sensing of the electrical parameter is prevented from overlapping the active recharge pulses.

20. The non-transitory machine-readable medium of claim 16, wherein the electrical stimulation is delivered on a first channel and the electrical parameter is sensed on a second channel.

* * * * *